US006939377B2

(12) United States Patent
Jayaraman et al.

(10) Patent No.: US 6,939,377 B2
(45) Date of Patent: Sep. 6, 2005

(54) COATED VASCULAR GRAFTS AND METHODS OF USE

(75) Inventors: Ramesh B. Jayaraman, Fremont, CA (US); Christofer T. Christoforou, Pleasanton, CA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 09/933,256

(22) Filed: Aug. 20, 2001

(65) Prior Publication Data

US 2002/0065552 A1 May 30, 2002

Related U.S. Application Data

(60) Provisional application No. 60/226,897, filed on Aug. 23, 2000, and provisional application No. 60/238,469, filed on Oct. 10, 2000.

(51) Int. Cl.[7] .................................................. A61F 2/06
(52) U.S. Cl. ...................................... 623/1.46; 623/1.49
(58) Field of Search ............................... 623/1.44–1.53

(56) References Cited

U.S. PATENT DOCUMENTS

| | | | |
|---|---|---|---|
| 2,900,644 A | | 8/1959 | Rosenberg et al. |
| 3,562,352 A | * | 2/1971 | Nyilas ........................ 525/440 |
| 3,562,820 A | | 2/1971 | Braun |
| 3,700,380 A | | 10/1972 | Kitrilakais |
| 3,789,828 A | | 2/1974 | Schulte |
| 3,862,452 A | | 1/1975 | Wichterle et al. |
| 4,131,604 A | | 12/1978 | Szycher |
| 4,173,689 A | | 11/1979 | Lyman et al. .................. 521/64 |
| 4,304,010 A | | 12/1981 | Mano |
| 4,306,318 A | | 12/1981 | Mano et al. |
| 4,334,327 A | | 6/1982 | Lyman et al. |
| 4,355,426 A | | 10/1982 | MacGregor ..................... 3/1.4 |

(Continued)

FOREIGN PATENT DOCUMENTS

| | | | |
|---|---|---|---|
| EP | 0 448 840 A2 | 10/1991 | .......... A61L/31/00 |
| EP | 0 448 840 A3 | 10/1991 | .......... A61L/31/00 |
| GB | 2 140 438 A | 11/1984 | .......... C08L/75/04 |
| WO | WO 96/30060 | 10/1996 | .......... A61L/27/00 |
| WO | WO 98/27895 | 7/1998 | ............. A61F/2/06 |
| WO | WO 00/10487 A | 3/2000 | ............. A61F/2/06 |
| WO | WO 00/27897 A | 5/2000 | .......... C08G/18/10 |

OTHER PUBLICATIONS

Thoratec Laboratories "Thoralon Technology" May 6, 1999, http://web.archive.org/web/19990506175502/www.thoratec.com/product/fr_futur.htm.*

"*Thoratec–Thoralon*," advertisement, 2 pages (1999).

Matthew D. Phaneuf et al., "*Coating of Dacron vascular grafts with an ionic polyurethane: a novel sealant with protein binding properties*," 22 BIOMATERIALS, pp. 463–469 (2001).

(Continued)

*Primary Examiner*—Thomas Barrett
(74) *Attorney, Agent, or Firm*—Baker Botts L.L.P.

(57) ABSTRACT

A vascular graft, such as an AAA stent graft, includes a core zone of PET fabric with a non-porous coating comprising a polyurethane, such as Thoralon®, disposed on at least one surface. The coating provides a barrier to prevent short and long term leakage of fluids through the pores of the PET fabric core zone. A method for sealing the pores of a porous PET graft includes the step of coating at least one surface of said graft with at least one polyurethane, or mixtures and combinations thereof. Preferably, the coating is Thoralon®. A method for making a vascular prosthesis includes the steps of providing a core zone of PET fabric, and coating at least one surface of the core zone with at least one polyurethane, or mixtures and combinations thereof, such as Thoralon®. Finally, a method of repairing or treating a defective vessel includes the step of reinforcing or replacing the defective vessel with a graft according to the invention.

13 Claims, 1 Drawing Sheet

U.S. PATENT DOCUMENTS

| | | | |
|---|---|---|---|
| 4,459,252 A | 7/1984 | MacGregor | |
| 4,604,762 A | 8/1986 | Robinson | 623/1 |
| 4,623,347 A | 11/1986 | Kira | |
| 4,647,416 A | 3/1987 | Seiler, Jr. et al. | 264/118 |
| 4,675,361 A | 6/1987 | Ward, Jr. | 525/92 |
| 4,678,468 A | 7/1987 | Hiroyoshi | 623/1 |
| 4,687,482 A | 8/1987 | Hanson | |
| 4,695,281 A | 9/1987 | Miyata et al. | |
| 4,731,073 A | 3/1988 | Robinson | 623/1 |
| 4,743,258 A | 5/1988 | Ikada et al. | 623/1 |
| 4,784,659 A | 11/1988 | Fleckenstein et al. | 623/1 |
| 4,816,339 A | 3/1989 | Tu et al. | 428/421 |
| 4,828,561 A | 5/1989 | Woodroof | |
| 4,861,830 A | 8/1989 | Ward, Jr. | 525/92 |
| 4,892,544 A | 1/1990 | Frisch | |
| 4,957,508 A | 9/1990 | Kaneko et al. | |
| 4,996,054 A | 2/1991 | Pietsch et al. | |
| 5,017,664 A | 5/1991 | Grasel et al. | 525/454 |
| 5,019,090 A | 5/1991 | Pinchuk | |
| 5,100,422 A | 3/1992 | Berguer et al. | 606/151 |
| 5,104,400 A | 4/1992 | Berguer et al. | 264/132 |
| 5,108,424 A | 4/1992 | Hoffman, Jr. et al. | |
| 5,116,360 A | 5/1992 | Pinchuk et al. | |
| 5,126,181 A | 6/1992 | Figuly et al. | 428/64 |
| 5,152,782 A | 10/1992 | Kowligi et al. | 623/1 |
| 5,274,074 A | 12/1993 | Tang et al. | |
| 5,298,276 A * | 3/1994 | Jayaraman | 427/2.25 |
| 5,330,782 A | 7/1994 | Kanazawa | |
| 5,412,068 A | 5/1995 | Tang et al. | |
| 5,486,593 A | 1/1996 | Tang et al. | |
| 5,575,815 A | 11/1996 | Slepian et al. | |
| 5,589,563 A | 12/1996 | Ward et al. | 528/44 |
| 5,607,474 A | 3/1997 | Athanasiou et al. | |
| 5,713,907 A * | 2/1998 | Hogendijk et al. | 606/108 |
| 5,735,897 A | 4/1998 | Buirge | |
| 5,741,333 A | 4/1998 | Frid | 623/12 |
| 5,779,729 A | 7/1998 | Severini | |
| 5,782,907 A | 7/1998 | Frantzen et al. | 623/1 |
| 5,855,598 A * | 1/1999 | Pinchuk | 623/1.13 |
| 5,861,033 A | 1/1999 | Martakos et al. | |
| 5,863,627 A | 1/1999 | Szycher et al. | 428/36.8 |
| 5,891,558 A | 4/1999 | Bell et al. | |
| 5,948,875 A | 9/1999 | Liu et al. | 528/61 |
| 5,980,564 A | 11/1999 | Stinson | |
| 5,984,965 A | 11/1999 | Knapp et al. | |
| 6,013,099 A | 1/2000 | Dinh et al. | |
| 6,015,431 A | 1/2000 | Thornton et al. | 623/1 |
| 6,042,605 A | 3/2000 | Martin et al. | |
| 6,083,257 A | 7/2000 | Taylor et al. | |
| 6,096,070 A | 8/2000 | Ragheb et al. | |
| 6,156,064 A * | 12/2000 | Chouinard | 623/1.44 |
| 6,177,523 B1 | 1/2001 | Reich et al. | |
| 6,197,051 B1 | 3/2001 | Zhong | |
| 6,225,435 B1 | 5/2001 | Ito et al. | 528/76 |
| 6,241,774 B1 | 6/2001 | Shimizu | |
| 6,254,642 B1 | 7/2001 | Taylor | |
| 6,264,700 B1 | 7/2001 | Kilcoyne et al. | |
| 6,302,917 B1 | 10/2001 | Dua et al. | |
| 6,309,413 B1 | 10/2001 | Dereume et al. | |
| 2001/0002444 A1 | 5/2001 | Zilla et al. | |
| 2001/0049550 A1 | 12/2001 | Martin et al. | |

OTHER PUBLICATIONS

Donald J. Dempsey et al., "*Optimizing Sealing Technique for Dacron Vascular Grafts Using an Ionic Polyurethane: Potential Use as Hemodialysis Access Graft*," abstract of presentation at Surfaces in Biomaterials 2000, pp. 145–147 and 2 pp material relating to presentation date (Symposium held Aug. 30–Sep. 2, 2000).

Feng Wang, "*Polydimethylsiloxane Modification of Segmented Thermoplastic Polyurethanes and Polyureas*," dissertation submitted to the faculty of Virginia Polytechnic Institute and State University (Apr. 13, 1998).

Toshikazu Yoneyama et al., "*Short–Term In Vivo Evaluation of Small–Diameter Vascular Prosthesis Composed of Segmented Poly(etherurethane)/2–Methacryloyloxyethyl Phosphorylcholine Polymer Blend*," 43 J Biomed Mater Res, pp. 15–20 (Spring 1998).

Press Release dated Jun. 23, 1999, "FDA Advisory Committee Recommends Approval of Medtronic's Minimally–Invasive Therapy for Abdominal Aortic Aneurysms," printed Jul. 14, 2000 from http://www.medtronic.com/news/articles 19990624083518.html (3pp).

Press Release dated Sep. 28, 1999, "Medtronic AneuRx™ Stent Graft System for Treatment of Abdominal Aortic Aneurysms Receives FDA Approval," printed Jul. 14, 2000 from http://www.medtronic.com/news/articles/19990928-125025.html (3pp).

AneuRx–Patient Information p. 3, web page printed Jul. 14, 2000 from http://www.aneurx.com/patientinfo_3.html (1p).

AneuRx–Patient Information p. 6, web page printed Jul. 14, 2000 from http://www.aneurx.com/patientinfo_6.html (1p).

AneuRx–Patient Information p. 9, web page printed Jul. 14, 2000 from http://www.aneurx.com/patientinfo_9.html (1p).

Balko, et al., *Transfemoral Placement of Intraluminal Polyurethane Prosthesis for Abdominal Aortic Aneurysm*, Journal of Surgical Research, 40:305–309 (1986).

PCT International Search Report PCT/US 01/25880, mailed Apr. 12, 2002.

PCT International Search Report, PCT/US 01/20262, mailed May 7, 2002.

Database Medline 'Online!, US National Library of Medicine, access. No. 200511982, XP002196620, abstract of Farrar DJ, "Development of a Prosthetic Coronary Artery Bypass Graft," Heart Surgery Forum, 3:1, pp. 36–40, 2000.

* cited by examiner

180
COATED VASCULAR GRAFTS AND METHODS OF USE

CROSS REFERENCE TO RELATED APPLICATIONS

This application claims the benefit of U.S. Provisional Patent Application No. 60/226,897 entitled "Coated Vascular Grafts," filed Aug. 23, 2000, and U.S. Provisional Patent Application No. 60/238,469 entitled "Coated Vascular Grafts," filed Oct. 10, 2000.

BACKGROUND OF THE INVENTION

1. Field of the Invention

The present invention relates generally to vascular grafts. More particularly, the present invention relates to woven or porous PET (polyethylene terephthalate) grafts having unique polyurethane coatings to improve resistance to permeability, useful in applications such as endolumenal repair of abdominal aortic aneurysm.

2. Description of Related Art

Abdominal aortic aneurysm (AAA) is a leading cause of death in the United States, causing an estimated 15,000 mortalities each year. An abdominal aortic aneurysm is a bulge in the wall of the artery, usually a sequela of arteriosclerosis or the buildup of plaque on the inside of the artery. If untreated, the aneurysm may rupture, causing death.

One approach for the treatment of AAA involves invasive abdominal surgery. The abdomen is opened and the aneurysm is identified. The aorta is opened and a surgical graft is inserted into the aorta and sewn in place. The aorta is then closed over the graft. More recently, stent grafts have been used in less-invasive procedures. Stent grafts include a graft layer inside or outside a stent structure. The stent graft provides a graft layer to reestablish a flow lumen through the aneurysm and a stent structure to support the graft and to resist occlusion or stenosis. Stent grafts may be inserted via incisions in the groin and deployed at the aneurysm site using a delivery catheter. Once in place, the stent graft expands within the aorta, providing a path for blood flow and reinforcing the weakened vessel. Examples of stent grafts are described in U.S. Pat. No. 6,015,431 to Thornton, et al. and published PCT International Application WO 98/27895.

A variety of materials have been used for vascular repair including PET (woven and knitted), Teflon®, bovine vessels, cryopreserved vessels of human or animal origin and others. Whether a traditional or stent graft, because of the size of the vessel being reinforced and the pressures within the vessel, AAA grafts must be made of strong and compliant textiles. Dacron®, or the more generic name, polyethylene terephthalate (PET), is an accepted and commonly used material for vascular repair, particularly for large diameter vascular grafts (>6 mm in diameter).

PET grafts are made in a similar fashion to most textiles. Fibers are woven or knitted into a specific geometry and structure. The result is a very strong "fabric" but one which is porous. Because integrity against leakage of the graft is important, such vascular grafts are often preclotted to prevent leaking. Alternately, graft pores have been sealed with collagen and other materials. However, although collagen and other coatings may provide sealing to prevent initial blood losses, known coatings have not proven adequate for more long term needs (>1–3 months) or cases where fluid (e.g., serum or water) permeability is important. The permeability of grafts is a particular problem in PET grafts for endolumenal AAA repair. Because of the porous nature and insufficiency of currently available coatings, over time seepage develops between the PET grafts and the aorta. In the case of AAA, permeability of the graft to any fluid can lead to worsening of the aneurysm.

SUMMARY OF THE INVENTION

Therefore, a need has arisen for grafts that provide the strength and compliance of woven PET grafts, while at the same time providing necessary short and long term resistance against leakage through the pores of the fabric. The present invention overcomes the problem of leakage through the pores seen with known large bore PET grafts.

The present invention is directed to grafts, such as stent grafts, made of fabrics coated with unique polyurethanes, such as THORALON® biomaterial, manufactured by Thoratec Corporation, having a principle place of business in Pleasanton, Calif., which provide a compliant, strong and impermeable barrier. Grafts according to the invention are particularly useful for the repair of vascular defects in large vessels, such as AAA. However, grafts coated according to the invention are not limited to AAA repair, and may be used in a variety of applications, including vascular grafts (including endoluminal stent grafts) and vascular patches for any area of the body. Grafts according to the present invention provide good and physiologic biocompatibility, biostability, compliance, and strength.

In one embodiment of the invention, a vascular graft, such as an AAA stent graft, comprises a core zone or layer comprising a PET fabric. The core zone has a first surface and a second surface opposing the first surface. A non-porous or pore-free coating is disposed on at least the first surface. The coating comprises at least one polyurethane. Preferably the polyurethane is a polyurethane urea, and, most preferably, is THORALON® biomaterial. The coating provides a barrier to prevent fluids from leaking through the pores of the PET fabric core zone. The core zone is preferably configured for use in a vessel having an internal diameter of more than 2 mm, and, more preferably, is configured for use in an abdominal aorta having an internal diameter of more than 6 mm.

Another embodiment of the invention provides a method for sealing the pores of a porous PET graft comprising the step of coating at least one surface of the graft with a polymer composition to produce a pore-free coat on the surface. The graft is preferably configured for use in a vessel having an internal diameter of more than 2 mm and, more preferably, is configured for use in an abdominal aorta having an internal diameter of more than 6 mm. The polymer composition comprises at least one polyurethane. The polyurethanes are segmented and comprise a soft segment and a hard segment. Preferably, the polymer composition is THORALON® biomaterial.

Methods for forming a vascular graft are also provided. For example, another embodiment of the invention provides a method for making a vascular prosthesis comprising the steps of providing a core zone or layer comprising a PET fabric, the core zone having a first surface and a second surface opposing the first surface; and coating at least the first surface of the core zone with a polymer composition to produce a pore-free coat on the surface. As with the previous embodiment, the polymer composition comprises at least one polyurethane and, most preferably, is THORALON® biomaterial. The core zone is preferably configured for use in a vessel having an internal diameter of more than 2 mm. Preferably, the vascular graft is an AAA graft and the core zone is configured for use in an abdominal aorta having an internal diameter of more than 6 mm.

Another embodiment of the invention is directed to a method of repairing or treating a defective vessel in an individual, such as a vessel having an internal diameter of more than 2 mm, comprising reinforcing or replacing the defective vessel with a graft according to the invention.

Other objects, features, and advantages will be apparent to those skilled in the art in view of the following description of the preferred embodiments and the accompanying drawings.

BRIEF DESCRIPTION OF THE DRAWINGS

The present invention may be more readily understood with reference to the following drawing in which.

DESCRIPTION OF PREFERRED EMBODIMENTS

Figure 1:
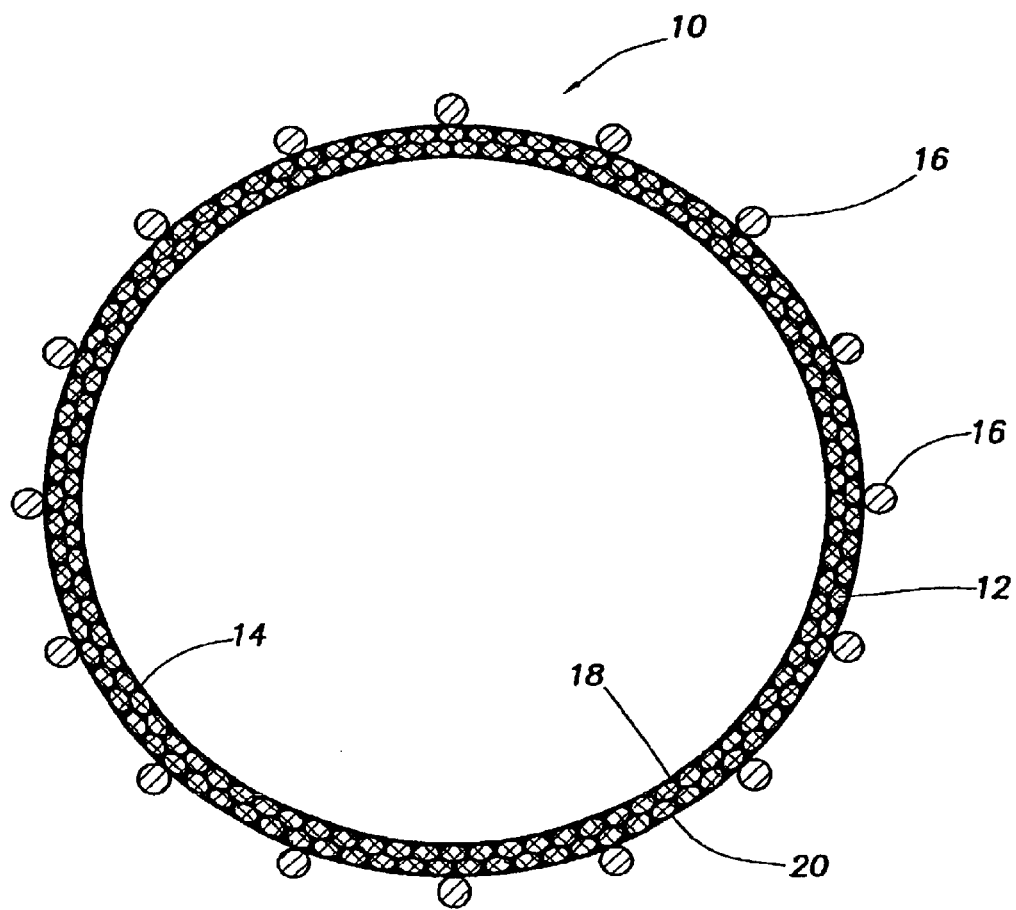
FIG. 1 is a cross-sectional view of the layered structure of a coated stent graft according to the invention.

The present invention is directed to vascular grafts made of porous fabrics, such as PET, coated with THORALON® biomaterial or other suitable polyurethanes, to prevent leakage of fluid through the pores of the graft. Specifically, the present invention uses blood-compatible polyurethanes, such as THORALON® biomaterial, as coatings for the blood-contacting textiles. Coated textiles according to the invention have improved impermeability (i.e., are less prone to allow leakage of fluids, such as serum or water, through the body of the graft, both long and short term). The present invention solves the problem of seepage between the graft and aorta through the pores of the fabric occurring with currently available coated PET grafts. The coatings of the invention may be used to coat other grafts, including, but not limited to, ePTFE (expanded polytetrafluoroethylene) grafts.

Because polyurethanes have very low water permeability, they can effectively seal a textile. Furthermore, polyurethanes, such as THORALON® biomaterial, possess a number of desirable properties such as biostability, compliance, biocompatibility, blood compatibility and strength, which are important in many vascular applications. As such, coated textiles according to the invention provide improved blood compatibility, as well as strong and compliant reinforcement or replacement of the diseased area. Accordingly, grafts coated according to the invention may be used in a variety of applications, including vascular grafts, stent grafts and vascular patches. Grafts according to the invention are particularly useful in the repair of AAA.

Grafts according to the invention provide a number of advantages. By using a polymer, preferably a polyether urethane urea such as THORALON® biomaterial, to seal the pores of a woven fabric graft, a blood compatible prosthesis is provided. Graft coatings need to be blood compatible because they come into contact with blood. In addition, the coatings of the invention adhere to the graft, seal the pore openings, and maintain their mechanical function (e.g., prevent seepage between the graft and artery) in vivo for a period of years.

The coating of the invention can perform the necessary sealing function at low thicknesses. Ideally, the profile of a graft must be thin to allow for the smallest possible endolumenal intervention. THORALON® biomaterial has been successfully applied as thinly as 4–5 microns. Depending on the size of the pore which needs to be sealed, even thinner applications may be achieved.

In view of this, the coatings of the invention are particularly useful for coating flat, uncrimped tubes of PET, to create a graft having a very thin profile, which is highly beneficial in endovascular applications.

By using the coatings of the invention, the pores of a porous PET stent graft have been effectively sealed, thereby reducing the permeability of a PET graft without altering the profile of the material by more than 50%. In addition to PET, grafts or patches made of other porous materials, such as ePTFE, may be effectively sealed.

Coatings according to the invention, such as THORALON® biomaterial coatings, not only provide a non-thrombogenic and an improved blood compatible lumen surface, but may also be used as a drug delivery vehicle (e.g., deliver a pharmacological agent) and as a surface-modifying coating to alter mechanical properties such as compliance and wear resistance. Also, THORALON® biomaterial may be applied as a foam to promote cell adhesion (such as endothelial cells) to form a neointima in all vascular graft applications.

A number of different coating materials may be applied to the porous graft fabric according to the invention to seal the pores and reduce permeability. These include polyurethane ureas, other polyurethanes, and mixtures of them. As used herein, the term "polyurethane" includes polyurethane urea as well as other polyurethanes. Coatings may also comprise the other materials as described below.

A preferred material for use as a coating according to the invention is THORALON® biomaterial. THORALON® biomaterial is a polyetherurethane urea blended with a siloxane containing surface modifying additive, and has been demonstrated to provide effective sealing of textile grafts. THORALON® biomaterial can be obtained from Thoratec Corporation, Pleasanton, Calif. Specifically, THORALON® biomaterial is a mixture of base polymer BPS-215 and an additive SMA-300 in dimethylacetamide (DMAC) solvent. The concentration of additive is preferably in the range of 0.5% to 5% by weight of the base polymer.

The BPS-215 component (Thoratec Corporation, Pleasanton, Calif. used in THORALON® biomaterial is a segmented polyether urethane urea containing a soft segment and a hard segment. The soft segment is made of polytetramethylene oxide (PTMO) and the hard segment is made of 4,4'-diphenylmethane diisocyanate (MDI) and ethylene diamine (ED).

The SMA-300 component is a polyurethane comprising polydimethylsiloxane as a soft segment and MDI and 1,4 butanediol as a hard segment. A process for synthesizing SMA-300 is described, for example, in U.S. Pat. No. 4,861,830 to Ward, Jr., at Column 14, Lines 17–41, and U.S. Pat. No. 4,675,361 to Ward, Jr., at Column 14, Lines 13–37, incorporated herein by reference.

THORALON® biomaterial is FDA approved for use in certain vascular applications and has been shown to be safe and effective in a variety of critical applications because it offers thromboresistance, high tensile strength, and superb flex life. THORALON® biomaterial has been shown to be biostable and useful in vivo in long term blood contacting applications requiring biostability and leak resistance for periods exceeding one year or more. THORALON® biomaterial has been shown to reduce platelet deposition and binding on blood contacting surfaces of extracorporeal circuits in patients undergoing cardiopulmonary bypass. Because of its flexibility, THORALON® biomaterial is particularly beneficial in larger vessels, such as the abdominal aorta, where elasticity and compliance is essential.

THORALON® biomaterial' lower water absorption contributes to enhanced in vivo stability, while its lower critical surface tension and longer Lee White Clotting Times demonstrate improved blood compatibility and thromboresistance (Table 1).

TABLE 1

Physical Properties of Thoralon ® in Comparison to Biomer

| Physical Properties | Biomer | Thoralon ® |
|---|---|---|
| Water Absorption | 4.1% wt gain | 1.8% wt. gain |
| Critical Surface Tension | 27.8 dynes/cm | 19.8 dynes/cm |
| Lee White Clotting Times | 29.1 minutes | 37 minutes |

In addition to THORALON®, biomaterial other polyurethane ureas may be used to coat the fabric component of the graft. For example, BPS-215 with a capping ratio (MDI/PTMO mole ratio) ranging from about 1.0 to about 2.5 may be used. Such polyurethane ureas preferably comprise a soft segment, and a hard segment comprising a diisocyanate and diamine. For example, polyurethane ureas with soft segments such as polyethylene oxide, polypropylene oxide, polycarbonate, polyolefin, polysiloxane (e.g., polydimethylsiloxane), and other polyether soft segments made from higher homologous series of diols may be used. Mixtures of any of the soft segments may also be used. The soft segments may also have either alcohol or amine end groups. The molecular weight of the soft segments may vary from about 500 to about 5,000 g/mole, and preferably is about 2,000 g/mole.

The diisocyanate used as a component of the hard segment may be represented by the formula OCN-R-NCO. R may be aliphatic, aromatic, cycloaliphatic or aromatic-aliphatic. Representative diisocyanates useful in the invention include, but are not limited to, tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

Suitable diamines useful as a component of the hard segment include aliphatic, aromatic and aliphatic-aromatic amines. For example, useful diamines include, but are not limited to, ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain nitrogen, oxygen or halogen.

In addition to polyurethane ureas, other polyurethanes (preferably having a chain extended with diols) may be used to coat the fabric of the graft. Polyurethanes modified with cationic, anionic and aliphatic side chains may also be used (see, e.g., U.S. Pat. No. 5,017,664 to Grasel, at Column 1, Lines 57–63, and Column 8, line 60–Column 11, Line 27). Polyurethanes may have to be dissolved in solvents such as dimethyl formamide, tetrahydrofuran, dimethyacetamide, etc., or mixtures thereof.

The soft segments of these polyurethanes may be comprised of any of the soft segments mentioned above (including, but not limited to, polytetramethylene oxide, polyethylene oxide, polypropylene oxide, polycarbonate, polyolefin, polysiloxane (e.g., polydimethylsiloxane), other polyether soft segments made from higher homologous series of diols, and mixtures of these soft segments. The soft segments may have amine or alcohol end groups).

The hard segment may be comprised of any of the diisocyantes listed above (including, but not limited to, 4,4'-diphenylmethane diisocyanate, tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof).

The hard segment may be comprised of polyols. Polyols may be aliphatic, aromatic, aromatic-aliphatic or cycloaliphatic. Preferred polyols include, but are not limited to, ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, and mixtures thereof.

In addition, the polyurethanes may also be end-capped with surface active end groups, such as, for example, polydimethylsiloxane, fluoropolymers, polyolefin, polyethylene oxide, or other suitable groups, including, but not limited to, those described in U.S. Pat. No. 5,589,563 to Ward Jr. et al. (see, e.g., Examples 2, 3, 5 and 8, at Column 28, Line 60–Column 31, Line 22, of U.S. Pat. No. 5,589,563, incorporated herein by reference).

In addition to the foregoing polymers, other useful materials for coating porous grafts include silicone rubber, polyisobutylene copolymer, polyolefin, polyester, polyamide, amorphous polyamide and mixtures and combinations of the above. As will be clear to those of skill in the art, suitable solvents are used to make solutions of these materials. For example, silicone rubber may be dissolved in heptanes and toluene may be used for polyolefins.

FIG. 1 depicts a preferred embodiment of an AAA stent graft according to the invention. Referring to FIG. 1, AAA stent graft 10 comprises a cylindrical PET fabric core zone 12. A polyurethane coating 14 is disposed on the inner diameter 18 and outer diameter 20 of zone 12. As can be seen in FIG. 1, the polyurethane matrix preferably permeates or infiltrates the spaces between the woven fibers of fabric core zone 12. Reinforcing layer 16 is disposed on the outside of core zone 12 and coating 14. Reinforcing layer 16 preferably comprises a plurality of stent wires made of stainless steel, nickel titanium alloy, or another suitable material.

Accordingly, one embodiment of the invention is directed to a vascular graft comprising a core zone or layer made of a PET fabric. The core zone is preferably configured or shaped for use in a vessel or for repair of a vessel having an internal diameter of more than 2 mm. More preferably, the vessel has an internal diameter of more than 3 mm, and, most preferably, more than 6 mm. The core zone has a first surface and a second surface opposing the first surface. A first non-porous coating is disposed on the first surface. This coating comprises at least one polyurethane, and preferably comprises a polyurethane urea. Preferably, the core zone comprises woven or knitted PET.

The coated first surface is preferably the blood interface surface of the graft. Alternately, the coated first surface may be the artery/tissue interface surface. In other words, the coating may be applied to either surface of the graft.

A second coating may be applied to the opposite surface of the graft. Alternately, a first coating applied to one surface may permeate through and form a cover or second coating on the opposing surface of the graft. For example, polyurethane applied to the first surface to form the first coating may penetrate the core zone and form the second coating on the second surface.

Although the present invention provides for a biocompatible, leak-resistant graft using a single coating material, if desired, in an alternate embodiment, one surface may be coated with one type of material, and the opposite or same surface coated with another type of material.

The core zone may have any desired shape, such as a cylinder, a bifurcated/Y-shaped cylinder, or a substantially flat sheet for patches.

In a preferred embodiment, at least a portion of the core zone has a substantially cylindrical shape and is a graft having an internal diameter of greater than 2 mm, and, more preferably, greater than 3 mm. Even more preferably, the graft is a large bore graft, in which the internal diameter is greater than 6 mm and the outer diameter is greater than 6.1 mm. For example, the external diameter may be designed or configured to fit in a large bore vessel, such as an abdominal aorta of an adult human. Alternatively, it may be designed to fit within other vessels, such as a human femoral artery or carotid artery.

The first surface is preferably disposed on the inner surface of the cylindrical core zone, i.e., the first coating is on the inner diameter of the cylinder. Alternatively, the first surface may be disposed on the outer surface of the cylindrical core zone, i.e., the first coating may be on the outer diameter of the cylindrical core zone. If desired, the graft may have a coating on both surfaces, i.e., both the first and second surfaces. The coatings may be applied separately to each side or, as noted, when the first coating is applied to one surface, it may permeate through and form a second coating on the opposing surface of the graft.

The graft may be used in a variety of applications, including as a vascular graft, as a stent graft or as a vascular patch. The graft is particularly useful for large bore vessels having an internal diameter of 6 mm or more. In a preferred embodiment, the graft comprises an AAA stent graft such as an AneuRx™ graft, supplied by Medtronic, Inc., Minneapolis, Minn. Other grafts which may be used include, but are not limited to, Ancure® AAA grafts manufactured by Guidant Corporation (headquartered in Indianapolis, Ind.; with facilities in Menlo Park, Calif.). In this embodiment, the stent graft may further comprise a more rigid component, such as stent wire or other suitable component to provide structural support to the stent graft. Preferably, the reinforcement is made of stainless steel or nickel-titanium alloy.

The coating on the PET fabric core may be comprised of any of the various materials described. For example, the coating may comprise a polyether urethane urea blended with a siloxane containing a surface modifying additive. The coating may comprise a polyether urethane urea, which has a soft segment comprising polytetramethylene oxide (PTMO) and hard segment comprising 4,4'-diphenylmethane diisocyanate (MDI) and ethylene diamine.

In a preferred embodiment, the coating comprises THORALON® biomaterial. However, the coating may comprise one or more polyurethanes, or mixtures and combinations thereof. Preferably, the polyurethanes each comprise a soft segment and a hard segment. As discussed above, the soft segment may comprise one or mere compounds selected from the group consisting of polytetramethylene oxide, polyethylene oxide, polypropylene oxide, polycarbonate, polyolefin, polysiloxane (e.g., polydimethylsiloxane), polyether soft segments made from higher homologous series of diols, and mixtures and combinations thereof. The soft segments may also have either alcohol or amine end groups.

The hard segment is comprised of an isocyanate (preferably a diisocyanate) and an amine (preferably a diamine) or a polyol. Alternately, the hard segment may comprise an isocyanate and both an amine and a polyol. The isocyanate component of the hard segment may comprise one or more compounds selected from the group consisting of 4,4'-diphenylmethane diisocyanate (MDI), tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl2,4-diisocyanate, 4,4'-biphenylene diisocyanate, 3,3-dimethoxy-4,4'-biphenyl diisocyanate, and mixtures and combinations thereof. The amine component of the hard segment may comprise one or more compounds selected from the group consisting of ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, alkanol amines and diamines, and mixtures and combinations thereof. The polyol component of the hard segment may comprise one or more compounds selected from the group consisting of ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, and mixtures and combinations thereof.

Another embodiment of the invention is directed to a method for sealing the pores of a porous PET graft comprising the step of coating at least one surface of the grail with a polymer composition to produce a pore-free coat on the surface, the polymer composition comprising at least one polyurethane, or mixtures and combinations of polyurethanes, as described herein. The graft is preferably configured for use in a vessel or to repair a vessel having an internal diameter of more than 2 mm. More preferably, the vessel has an internal diameter of more than 3 mm, and, most preferably, more than 6 mm. Preferably, the graft comprises an AAA stent graft and the polymer composition comprises THORALON® biomaterial.

The invention is also directed to methods of making PET grafts having reduced permeability. In making such grafts, adhesion of the polyurethane to the textile is a critical parameter. To enhance adhesion, the textile may be pretreated by washing the textile in methylene chloride, acetone, or another suitable agent. Alternately, additives to the polyurethane may be used to promote effective bonding. Examples include, but are not limited to, THORALON® biomaterial with and without siloxane additive (SMA).

The coating can be applied in a variety of ways, including but not limited to, spraying, dipping, applying with rollers or brushes, or casting. These processes can be applied on a textile sheet, graft or final product construct (e.g., stented graft) to improve the functional performance of the product by reducing permeability. As noted, coating material applied to one side may permeate through and form a cover or coating on both surfaces of the graft.

In a preferred method, the coating applied to the graft is formed from a solution of polurethane that readily penetrates the graft. By using such solutions, no pressure is needed to get the coating to permeate into the pores of the graft.

As noted, the actual application of the different coatings of the invention may be accomplished in a number of ways. For example, the polymer composition may be applied using a brush, followed by heating the coated part in an oven while rotating the coated part to drive off the solvent. One or more coating layers may be applied to attain desirable thickness.

Alternately, the polymer composition may be sprayed onto the fabric core using a spray nozzle and the coating may be dried. Alternately, the core may be dip coated. Useful methods for dip coating and spray coating are described, for example, in U.S. Pat. No. 5,104,400 to Berguer et al.

If desired, the polymers may also be reacted in place. For example, two-component polyurethane or silicone rubber may be used. The coating may also be obtained by coating a suitable monomer, by itself or in a solvent on the fabric and polymerizing by thermal energy (heat) or high-energy light sources such as UV.

Accordingly, another embodiment is directed to a method for making a vascular prosthesis comprising providing a core zone or layer comprising a porous PET fabric, the core zone having a first surface and a second surface opposing the first surface; and coating at least the first surface of the core zone with a polymer composition (e.g., in slurry or solution form) to produce a first pore-free coat on the first surface. The core zone is preferably configured for use in a vessel or to repair a vessel having an internal diameter of more than 2 mm. More preferably, the vessel has an internal diameter of more than 3 mm, and, most preferably, more than 6 mm. The polymer composition may penetrate the core zone to produce a second coat on the second surface. Alternately, the second surface may be separately coated with the polymer composition. The polymer composition preferably comprises at least one polyurethane, or mixtures and combinations of polyurethanes, as described herein.

The step of coating may be accomplished by spraying at least one layer of the polymer composition on the first surface of the core zone and allowing the layer to dry. These steps may be repeated one or more times until the desired thickness is obtained. Alternatively, the step of coating may comprise applying the polymer composition to the first surface with a brush or roller. In this embodiment, the method may further comprise heating the coated surface to drive off any solvent. Alternatively, the step of coating may comprise dipping the core zone in a slurry of the polymer composition one or more times.

Regardless of the application process, drying of the coating is optimally accomplished at temperatures in a range of about 30° C. to about 150° C., and most preferably, at a temperature about 60° C.

In another variation, the step of coating may comprise coating at least the first surface with a monomer and polymerizing the monomer to form the polymer composition by thermal energy or high energy light.

Optionally, the method may further comprise pretreating the core zone by washing in methylene chloride or another suitable agent. If desired, one or more additives may be added to the polymer composition to enhance bonding of the polymer composition to the core zone.

Another embodiment of the invention is directed to a method of repairing or treating a defective vessel in an individual, such as a vessel having an internal diameter of more than 2 mm, comprising reinforcing or replacing the defective vessel with a graft according to the invention. The individual may be any animal, and is preferably a mammal, such as a human. The defective vessel may be any vessel, and is preferably a large bore vessel, such as the abdominal aorta of a human.

The following examples are offered to illustrate embodiments of the invention, and should not be viewed as limiting the scope of the invention.

EXAMPLES

Example 1

Water Permeability Test

In this example, the water permeability of uncoated graft fabric was compare to fabrics coated with THORALON® biomaterial. Testing was performed in accordance with Association of the Advancement of Medical Instrumentation, ANSI/AAMI VP20, 1994, with the exception of the diameter of the opening, as discussed below. The uncoated fabric tested was made of polyester, and more specifically, was fabric from an AAA graft (AneuRx™ polyester fabric graft, supplied by Medtronic, Inc., Minneapolis, Minn.). This same fabric was also coated with about a 12 micron layer of THORALON® biomaterial on both sides.

The samples were tested as follows. Approximately 1 $cm^2$ of fabric was cut and sandwiched between two acrylic plates containing a circular opening at the center measuring 0.1257 $cm^2$ in diameter. The plates were then connected to (sandwiched between) two acrylic tubes having the same radius inner diameter. One of the tubes was connected to a water column that provided a constant pressure of 100±1 mm Hg. The water was allowed to flow through the fabric for 2 minutes, and the water passing through the fabric was collected. The collected quantity of water was determined. The results shown in Table 2 are an average of triplicate analysis and are reported in terms of $cc/min/cm^2$.

TABLE 2

| Material | Flow Rate ($cc/min/cm^2$) |
| --- | --- |
| uncoated fabric | 240 ± 8 |
| Thoralon ® coated fabric | no flow |

As can be seen from Table 2, there was no flow of water through the THORALON® biomaterial coated fabric, confirming that THORALON® biomaterial coatings can dramatically improve the water permeability of porous graft fabrics.

Although the invention has been described with respect to preferred embodiments, the foregoing description and examples are intended to be merely exemplary of the invention. The true scope and spirit of the invention is not intended to be limited by the foregoing description and examples, but instead is intended to be commensurate with the scope of the following claims. Variations and modifications on the elements of the claimed invention will be apparent to persons skilled in the art from a consideration of this specification or practice of the invention disclosed herein.

What is claimed is:

1. A vascular graft comprising:
   a core zone comprising a PET fabric, said core zone having a first surface and a second surface opposing said first surface, wherein the first surface is a blood interface surface; and
   a first non-porous coating disposed on said first surface and permeating into at least a portion of said core zone, such that said at least one portion of said core zone is impermeable, wherein said first coating comprises at least one polyurethane; wherein the coating comprises a polyurethane urea, wherein said first coating has a thickness of about 12 µm.

2. A vascular graft comprising:
   a core zone comprising a PET fabric, said core zone having a first surface and a second surface opposing said first surface, wherein the first surface is a blood interface surface; and a first non-porous coating disposed on said first surface and permeating into at least a portion of said core zone, such that said at least one portion of said core zone is impermeable, wherein said first coating comprises at least one polyurethane; wherein the coating comprises a polyetherurethane urea blended with a siloxane containing a surface modifying additive, wherein said first coating has a thickness of about 12 µm.

3. A vascular graft comprising:
   a core zone comprising a PET fabric, said core zone having a first surface and a second surface opposing said first surface, wherein the first surface is a blood interface surface; and
   a first non-porous coating disposed on said first surface and permeating into at least a portion of said core zone, such that said at least one portion of said core zone is impermeable, wherein said first coating comprises at least one polyurethane; wherein said at least one polyurethane comprises a soft segment and a hard segment, wherein said first coating has a thickness of about 12 µm.

4. The graft of claim 3 wherein the soft segment has a molecular weight of about 2,000 g/mole.

5. The graft of claim 3 wherein the soft segment comprises one or more compounds selected from the group consisting of polyethylene oxide, polypropylene oxide, polytetramethylene oxide, polycarbonate, polyolefin, polysiloxane, polyether soft segments made from higher homologous series of diols, and mixtures and combinations thereof.

6. The graft of claim 3 wherein the hard segment comprises one or more compounds selected from the group consisting of 4,4'-diphenylmethane diisocyanate, tetramethylene diisocyanate, hexamethylene diisocyanate, trimethylhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl2,4-diisocyanate, 4,4'-biphenylene diisocyanate, 3,3-dimethoxy-4,4'-biphenyl diisocyanate, ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, alkanol amines and diamines, ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, and mixtures and combinations thereof.

7. The graft of claim 3 wherein said coating comprises a polyether urethane urea, and wherein said soft segment comprises polytetramethylene oxide (PTMO) and said hard segment comprises 4,4'-diphenylmethane diisocyanate (MDI) and ethylene diamine.

8. A vascular graft comprising:
   a core zone comprising a PET fabric, said core zone having a first surface and a second surface opposing said first surface, wherein the first surface is a blood interface surface; and
   a first non-porous coating disposed on said first surface and permeating into at least a portion of said core zone, such that said at least one portion of said core zone is impermeable, wherein said first coating comprises at least one polyurethane; wherein the coating comprises a polyurethane urea, wherein said first coating has a thickness in a range of about 4 µm to about 5 µm.

9. A vascular graft comprising:
   a core zone comprising a PET fabric, said core zone having a first surface and a second surface opposing said first surface, wherein the first surface is a blood interface surface; and
   a first non-porous coating disposed on said first surface and permeating into at least a portion of said core zone, such that said at least one portion of said core zone is impermeable, wherein said first coating comprises at least one polyurethane; wherein the coating comprises a polvetherurethane urea blended with a siloxane containing a surface modifying additive, wherein said first coating has a thickness in a range of about 4 µm to about 5 µm.

10. A vascular graft comprising:
    a core zone comprising a PET fabric, said core zone having a first surface and a second surface opposing said first surface, wherein the first surface is a blood interface surface; and
    a first non-porous coating disposed on said first surface and permeating into at least a portion of said core zone, such that said at least one portion of said core zone is impermeable, wherein said first coating comprises at least one polyurethane; wherein said at least one polyurethane comprises a soft segment and a hard segment, wherein said first coating has a thickness in a range of about 4 µm to about 5 µm.

11. The graft of claim 10 wherein the soft segment has a molecular weight of about 2000 g/mole.

12. The graft of claim 10 wherein the soft segment comprises one or more compounds selected from the group consisting of polyethylene oxide, polypropylene oxide, polytetramethylene oxide, polycarbonate, polyolefin, polysiloxane, polyether soft segments made from higher homologous series of diols, and mixtures and combinations thereof.

13. The graft of claim 10 wherein the hard segment comprises one or more compounds selected from the group consisting of 4,4'-diphenylmethane diisocyanate, tetramethylene diisocyanate, hexamethylene diisocyanate, trimethylhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl2,4-diisocyanate, 4,4'-biphenylene diisocyanate, 3,3-dimethoxy-4,4'-biphenyl diisocyanate, ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, alkanol amines and diamines, ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, and mixtures and combinations thereof.

\* \* \* \* \*